US00PP36335P3

(12) United States Plant Patent
Fotinos

(10) Patent No.: US PP36,335 P3
(45) Date of Patent: Dec. 24, 2024

(54) ***HYDRANGEA* PLANT NAMED 'HYD15'**

(50) Latin Name: *Hydrangea macrophylla*
Varietal Denomination: HYD15

(71) Applicant: Peter Fotinos, Santa Barbara, CA (US)

(72) Inventor: Peter Fotinos, Santa Barbara, CA (US)

( * ) Notice: Subject to any disclaimer, the term of this patent is extended or adjusted under 35 U.S.C. 154(b) by 0 days.

(21) Appl. No.: 18/445,022

(22) Filed: Mar. 9, 2023

(65) Prior Publication Data

US 2024/0306520 P1 Sep. 12, 2024

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP16,441 P2 * 4/2006 Arts ..... A01H 6/48
Plt./250

* cited by examiner

*Primary Examiner* — June Hwu

(57) ABSTRACT

A new *Hydrangea macrophylla* pink or blue with attractive flower. This variety propagates from soft wood cuttings and is stable in subsequent generations and is used for year-round production in greenhouse for flowering pot plant production.

4 Drawing Sheets

Latin name of the genus and species: *Hydrangea macrophylla.*

Variety denomination: 'HYD15'.

BACKGROUND OF THE INVENTION

The two *Hydrangea macrophylla* parents were crossed in the fall of 2016 to breed the new *Hydrangea* plant 'HYD15'. The two parents were female unnamed seedling blue bicolor (not patented in the U.S.) x male 'Mathilda Gutges' blue (not patented in the U.S.) The female parent was the unnamed seedling blue bicolor with blue and white flowers and large inflorescences. 'Mathilda Gutges' is a named variety of *Hydrangea* with dark blue flowers and large inflorescences. 'HYD15' has medium size inflorescences which are light blue or pink. It may be distinguished from its pollen parent by the lighter flower color, the faster finish time, and the more numerous flowers it has blooming at one time. It may be distinguished from the female parent by the color of its flower the more numerous flowers and the plant habit a full inflorescence. The plant was reproduced in Santa Barbara, CA in an indoor greenhouse environment.

BRIEF SUMMARY OF THE INVENTION

Initial asexual reproduction was done of 'HYD15' by cuttings in Santa Barbara, California, U.S.A. The reproduction was conducted in a controlled greenhouse environment.

Have here proven that the foregoing and all after characteristics and distinctions come true to form and are established in succeeding propagations. *Hydrangea* 'HYD15' is a low vigorous compact *Hydrangea* for pot production. The inflorescence bloom will last about 4-8 weeks in the container. The objective of the hybridization was to find a unique variety with:

1. Uniform and abundant flowers with good keepability for the floral industry
2. Attractive long-lasting foliage
3. Suitable for soft wood propagation
4. Remontant
5. Resistance to heat distortion during flower formation common with Dutch bred *Hydrangeas.*

'HYD15' has proven to be all the above making flowers year-round in the greenhouse structure in Santa Barbara, California with no distortion over the trial periods. 'HYD15' will rebloom within the same year without vernalization. We are not aware of any other varieties with these characteristics.

BRIEF DESCRIPTIONS OF THE DRAWINGS

The accompanying color illustrations show as true as is reasonable to obtain in color photographs of this type, the typical characteristics of the buds, flowers leaves, stems of 'HYD 15'. The plant photographed below is 44-46 weeks old. The *Hydrangeas* in photographs 1 and 6 are treated with aluminum sulfate to create a blue color. Specifically illustrated in the drawings:

On Sheet 1/4
1: Development of blue flowers
2: Development of pink flower
3: Tip of young shoot
4: Upper side of leaf
5: Underside of leaf
On Sheet 2/4
6: Blue flower head fully unfolded.
On Sheet 3/4
7: Pink flower head unfolded.
On Sheet 4/4
8: Flower bare corymb
9: Corymb starting to unfold.

DETAILED BOTANICAL DESCRIPTION OF THE VARIETY

The following is a detailed description of the *Hydrangea* plant: *Hydrangea macrophylla* 'HYD15'.

The following observations, measurements, values, and comparisons describe plants grown in glass houses in Santa Barbara, California, U.S.A.

The age of observed plants were 44 to 48 weeks old produced in a 10 cm diameter pot.

Environmental conditions were between 34-90 degrees Fahrenheit. Ten to twenty hours a day with assimilation light. Light levels of 600-6,000 foot candles. The relative humidity has been 50 to 85%. Plants have been regulated with PGR to modify plant shape and height.

Color References are using The Royal Horticultural Society (London, England) Colour Chart, 2019 (reprint). For comparison with existing *Hydrangea* 'Early Blue' ('200749077', U.S. Plant Pat. No. 16,441 P2).

CHART 1

| Chart 1: | HYD15 | Early Blue |
|---|---|---|
| Sepal Color Upper Surface | 111A blue green veins 100B purple blue light reddish N78D or deep purplish pink N57B to D | Strong Purplish Blue 95C |
| Sepal Color Reverse Surface | Moderate Purplish Pink 68 D blue green group 111A venation 111D pale blue | Violet blue group 98C light blue |
| Sterile Flower Count | 200 to 270 | 150-200 |
| Sepal Count | 4-7 | 4 |

Parents: The two parents were crossed in the fall of 2016.

The two parents were unnamed seedling blue bicolor and 'Mathilda Gutges' blue.

Classification:

*Botanical.*—*Hydrangea macrophylla.*

*Commercial.*—Pot *Hydrangea.*

Plant:

*Plant growth.*—Vigorous upright growth with compact habit when grown as a 11 cm average plant height is 25 to 30 cm average width is 20 cm. When grown in a 16 cm pot average height is 42 to 47 cm width is 30-35 cm. From unrooted cutting to finishing in either pot is 42 to 46 weeks depending on cultural practices and environmental conditions the habit is rounded. Production time is generally 44 to 48 weeks from unrooted cutting to finished plant depending on temperature light level and time of year. Pink flowers have soil pH over 6 and blue flowers are 4.5 pH to 5 pH with 20 ppm of aluminum sulfate added to the irrigation water.

Stem:

*Color.*—Stem color young wood green group yellowish green 134C internode base color on stem red purple group strong purplish red 67A stem. Hard wood grey-brown group strong yellow brown 199D and darker areas with dark greyish yellow brown N199B.

*Lenticels.*—On stems red purple group strong purplish red 67A 30-60 between nodes ovate vertical 0.3 to 0.5 mm.

*Surface.*—Young Wood: Smooth Older Wood: Smooth.

*Stem diameter.*—Diameter 4-5 mm.

*Internode length.*—20-50 mm.

*Vegetation.*—Dense.

*Blooming.*—Abundant.

*Aptitude to bear fruit.*—Poor.

*Resistance to diseases.*—Above normal disease resistance: Powdery and Downy Mildews, *Pythium, Botrytis* in Santa Barbara growing conditions.

*Winter hardiness & drought/heat tolerance.*—Not tested for winter hardiness. Drought tolerance.

I claimed:

1. A new and distinct variety of *Hydrangea* plant named 'HYD15', substantially as illustrated and described herein will develop flowers year-round under short day conditions at a temperature of 52° F. to over 90° F. (11° C. to 32° C.), the variety is remontant, which means it will bloom again after the first flower is cut off without vernalization.

* * * * *

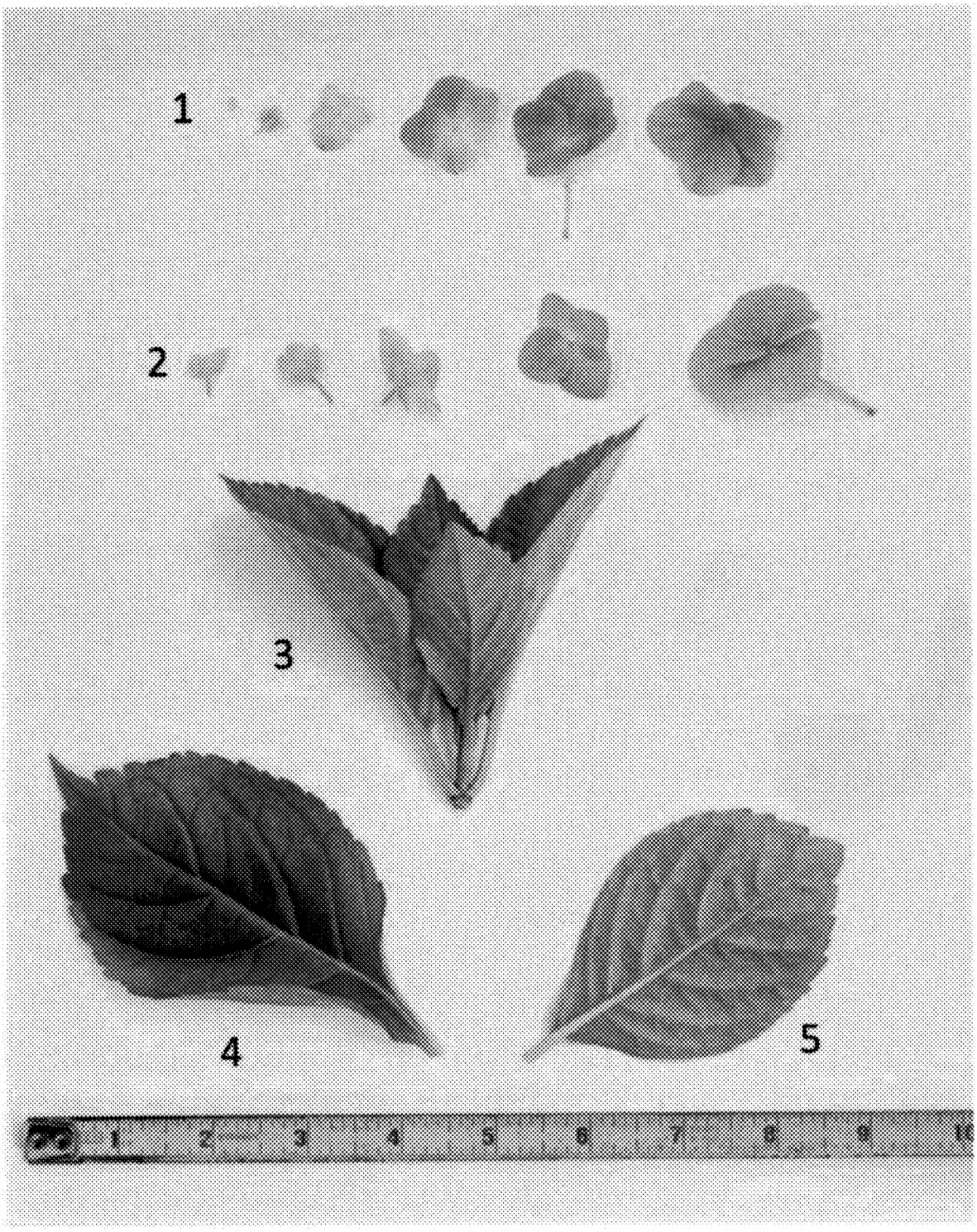
1
2
3
4
5
1 2 3 4 5 6 7 8 9 10

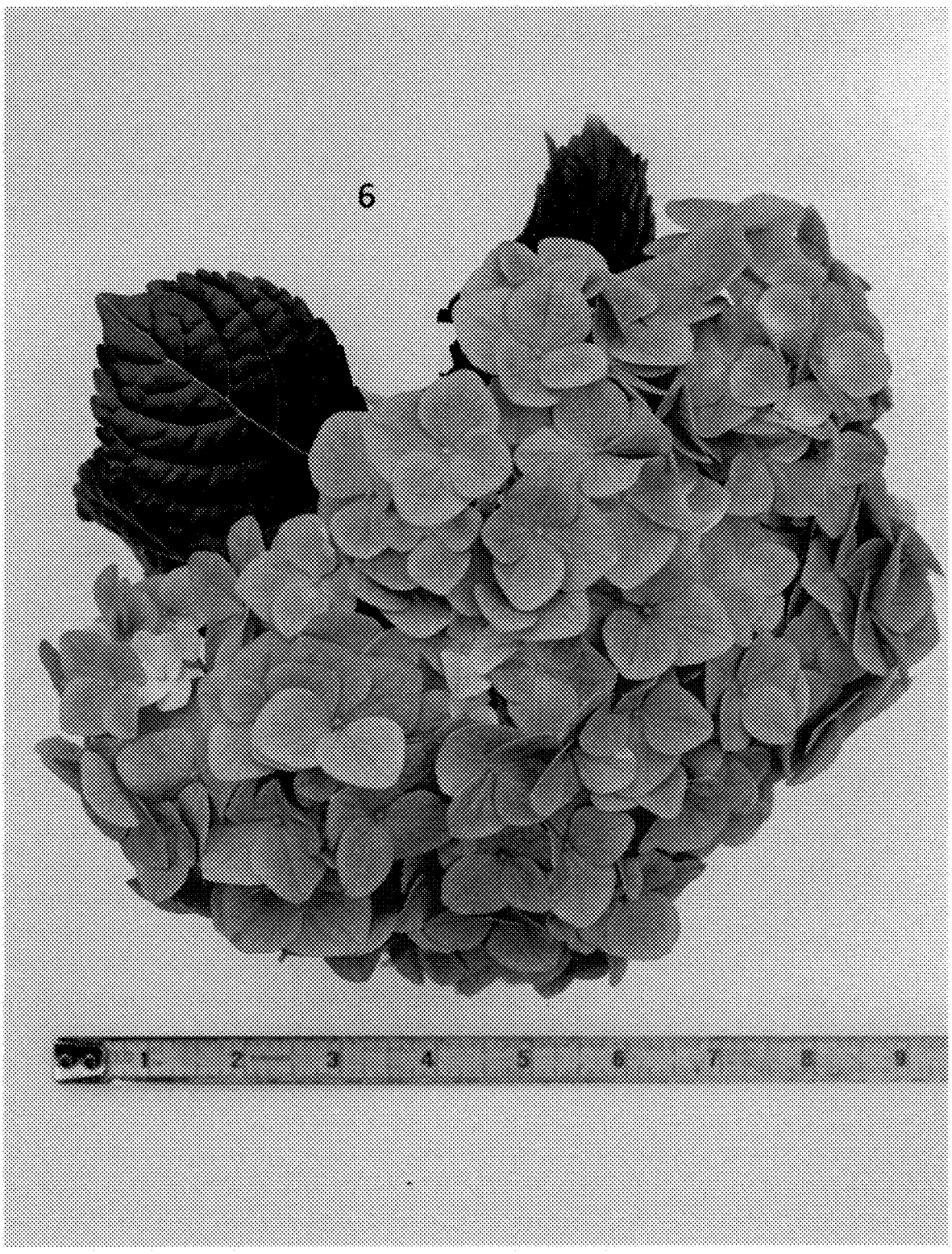
6
1
2
3
4
5
6
7
8
9

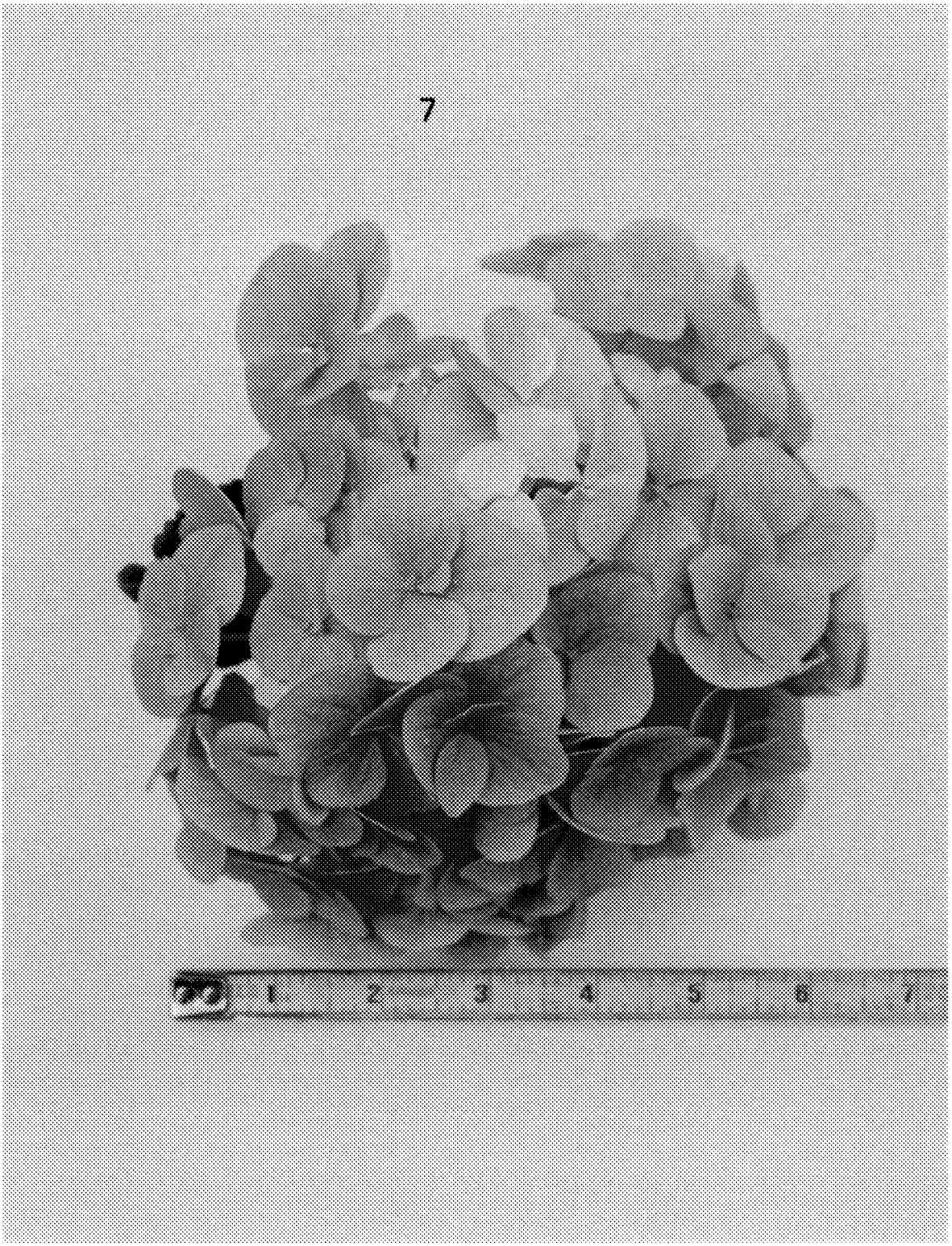
7
1
2
3
4
5
6
7

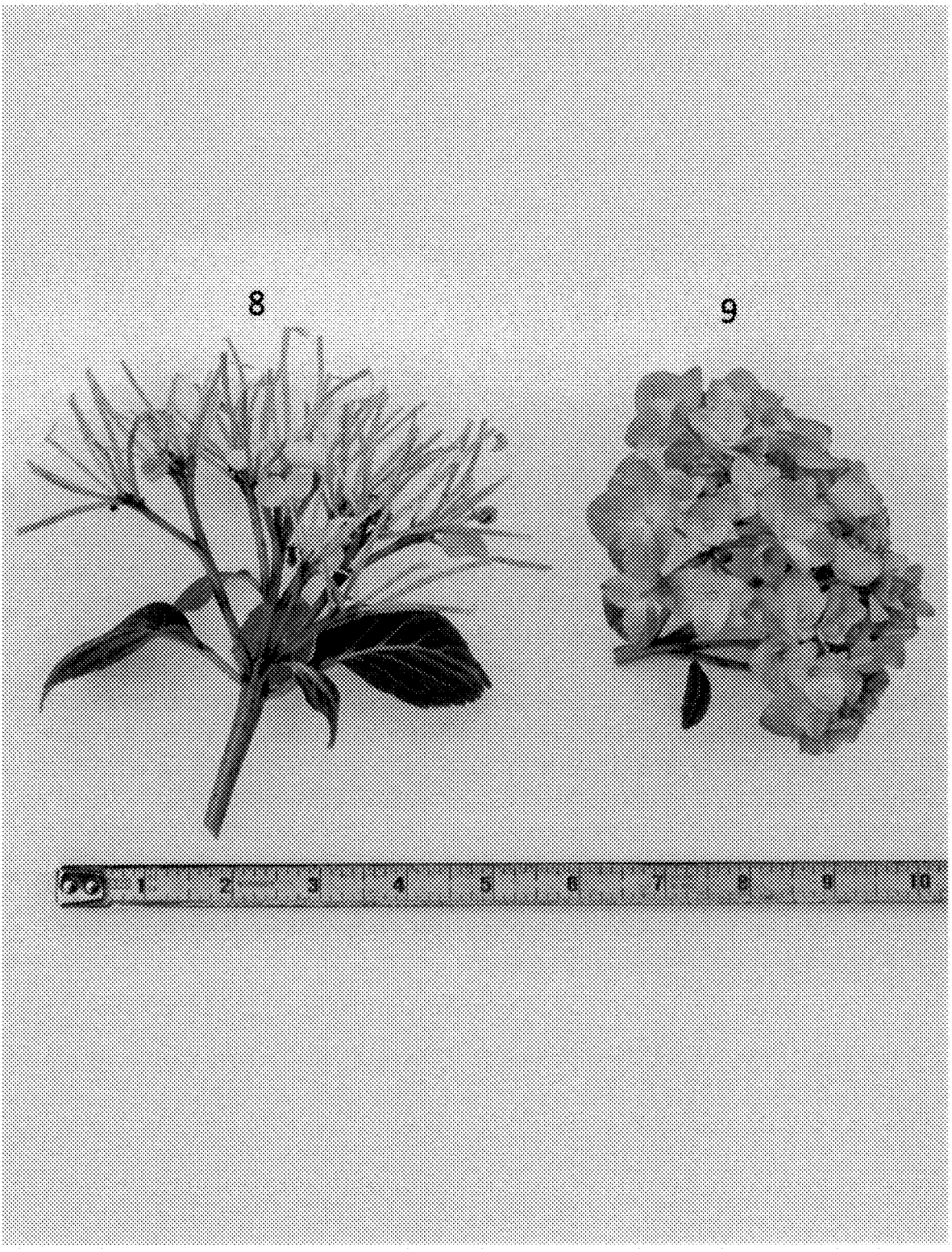
8
9
1
2
3
4
5
6
7
8
9
10